(12) United States Patent
Schwimmer

(10) Patent No.: US 10,390,857 B1
(45) Date of Patent: Aug. 27, 2019

(54) AIRWAY IMPLANT DELIVERY DEVICE

(71) Applicant: The Snoring Center, Dallas, TX (US)

(72) Inventor: Craig Schwimmer, Dallas, TX (US)

(73) Assignee: The Snoring Center, Dallas, TX (US)

( * ) Notice: Subject to any disclaimer, the term of this patent is extended or adjusted under 35 U.S.C. 154(b) by 0 days.

(21) Appl. No.: 15/981,271

(22) Filed: May 16, 2018

Related U.S. Application Data

(60) Provisional application No. 62/663,130, filed on Apr. 26, 2018.

(51) Int. Cl.
*A61F 2/20* (2006.01)
*A61F 5/56* (2006.01)
*A61B 17/24* (2006.01)
*A61B 17/34* (2006.01)

(52) U.S. Cl.
CPC .......... *A61B 17/3468* (2013.01); *A61B 17/24* (2013.01); *A61F 2/20* (2013.01); *A61F 5/566* (2013.01)

(58) Field of Classification Search
USPC .......................... 128/846–848, 898; 606/185
See application file for complete search history.

(56) References Cited

U.S. PATENT DOCUMENTS

| | | |
|---|---|---|
| 6,250,307 B1 | 6/2001 | Conrad et al. |
| 6,390,096 B1 | 5/2002 | Conrad et al. |
| 6,401,717 B1 | 6/2002 | Conrad et al. |
| 6,415,796 B1 | 7/2002 | Conrad et al. |
| 6,450,169 B1 | 9/2002 | Conrad et al. |
| 6,453,905 B1 | 9/2002 | Conrad et al. |
| 6,502,574 B2 | 1/2003 | Steven et al. |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,523,543 B2 | 2/2003 | Conrad et al. |
| 6,578,580 B2 | 6/2003 | Conrad et al. |
| 6,601,584 B2 | 8/2003 | Knudson et al. |
| 6,601,585 B1 | 8/2003 | Conrad et al. |
| 6,626,181 B2 | 9/2003 | Knudson et al. |
| 6,634,362 B2 | 10/2003 | Conrad et al. |
| 6,848,447 B2 | 2/2005 | Conrad et al. |
| 6,899,105 B2 | 5/2005 | Krueger et al. |
| 7,028,691 B2 | 4/2006 | Knudson et al. |
| 7,036,515 B2 | 5/2006 | Conrad et al. |
| 7,047,979 B2 | 5/2006 | Conrad et al. |
| 7,063,089 B2 | 6/2006 | Knudson et al. |
| 7,100,613 B2 | 9/2006 | Conrad et al. |
| D536,792 S | 2/2007 | Krueger et al. |
| 7,237,553 B2 | 7/2007 | Knudson et al. |
| 7,255,109 B2 | 8/2007 | Knudson et al. |
| 2005/0065615 A1 | 3/2005 | Krueger et al. |
| 2005/0154412 A1 | 7/2005 | Krueger et al. |
| 2009/0318875 A1 | 12/2009 | Friedman |
| 2014/0243975 A1* | 8/2014 | Saidi .................. A61F 5/08 623/10 |
| 2015/0088166 A1 | 3/2015 | Krespi et al. |
| 2016/0220411 A1 | 8/2016 | Krespi et al. |

FOREIGN PATENT DOCUMENTS

CN        1969771 B        7/2011

* cited by examiner

*Primary Examiner* — Yashita Sharma
(74) *Attorney, Agent, or Firm* — Bill R. Naifeh

(57) ABSTRACT

Embodiments of a delivery device for inserting multiple implants into an airway of a patient.

33 Claims, 15 Drawing Sheets

AIRWAY IMPLANT DELIVERY DEVICE

CROSS REFERENCE TO RELATED APPLICATIONS

This patent application incorporates by reference several patents. These patents include U.S. Pat. No. 6,250,307 to Conrad et al. dated Jun. 26, 2001 which describes (along with other embodiments) elongated implants for placement in the soft palate. In one embodiment, three such implants are placed in the soft palate. U.S. Pat. No. 6,578,580 to Conrad et al. dated Jun. 17, 2003 describes a needle (which may have a perforated distal tip) for delivery of an implant. The implant may be preloaded into the needle. In U.S. Pat. No. 6,523,542 to Metzger, et al. dated Feb. 25, 2003, an implant is described as a sheet of felt or similar material delivered through a needle. U.S. Pat. No. 6,513,530 to Knudson et al. dated Feb. 4, 2003 describes the implant as a braid with welded ends near frayed ends. U.S. Pat. No. 6,431,174 to Knudson et al. dated Aug. 13, 2002 describes use of microbeads as implants as well as describing placement of implants in a pharyngeal wall or nasal area as well as a soft palate.

TECHNICAL FIELD

This invention is directed to an apparatus for treating an airway condition of a patient. More particularly, this invention is directed to an apparatus and/or a related kit for delivering an implant into tissue of a patient's airway.

BACKGROUND INFORMATION

Airway conditions such as snoring and obstructive sleep apnea ("OSA") have received increased scientific and academic attention. One publication estimates that up to 20% of the adult population snores habitually. Huang, et al., "Biomechanics of Snoring", Endeavour, p. 96-100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Treatments for snoring and sleep apnea, such as delivery systems for implants are known in the prior art, but they are relatively expensive. What is needed are improved delivery systems that are cost effective and minimize waste.

SUMMARY

In response to these and other problems, in one embodiment, there is handheld apparatus for use in treating an airway condition of a patient. The apparatus comprises driving mechanism and a cartridge wherein the cartridge includes multiple implants to be implanted into tissue of the patient. The use of a cartridge using multiple implants may result in less waste and expense.

These and other features, and advantages, will be more clearly understood from the following detailed description taken in conjunction with the accompanying drawings. It is important to note the drawings are not intended to represent the only aspect of the invention.

BRIEF DESCRIPTION OF THE DRAWINGS

FIGS. 12-14B are illustrations of a second embodiment of a delivery tool.

FIG. 14B is a horizontal sectional view of the delivery tool of FIG. 12A also in a loaded or second configuration.

DETAILED DESCRIPTION

Figure 1:
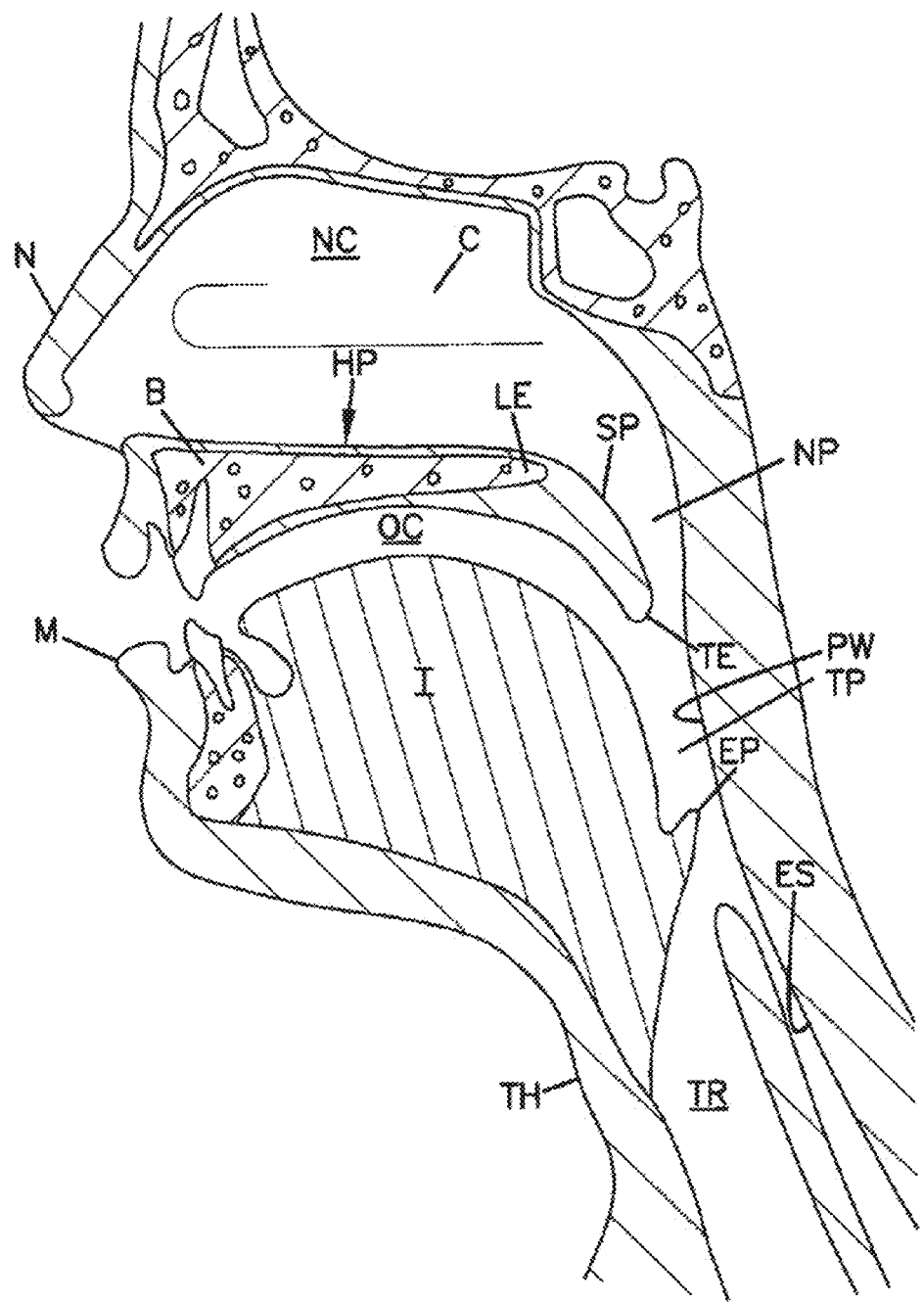
FIG. 1. is a cross-section schematic illustration of a naso-pharyngeal area of an untreated patient.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in the figures. The directions should not be read to imply actual directions used in any resulting invention or actual use. Under no circumstances, should such directions be read to limit or impart any meaning into the claims.

Figure 2:
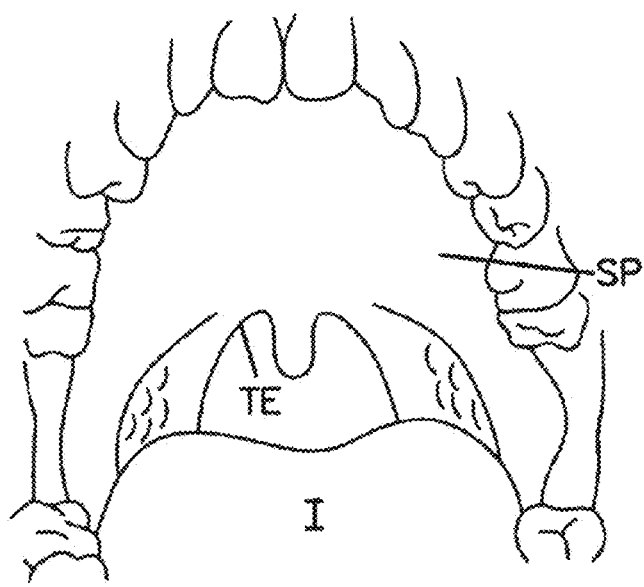
FIG. 2 is a schematic illustration of a soft palate viewed through an open mouth of the untreated patient of FIG. 1.

FIG. 1 shows, in cross-section, a naso-pharyngeal area of an untreated patient. FIG. 2 shows a soft palate SP viewed through an open mouth of the untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area (or airway) of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep as well as having nasal and palatal contributions.

As indicated above, most of the present disclosure will describe delivery mechanisms for placing a plurality of stiffening implants into the soft palate SP. However, it will be appreciated that aspects of the present invention is applicable to other regions of the naso-pharyngeal area including the nasal concha C and the pharyngeal wall PW. Also, aspects of the present invention is applicable to airway conditions such as OSA or snoring and is not intended to be limited to snoring although this indication will be most frequently referenced for purpose of illustration of the invention. Finally, aspects of the present invention can be used with different types of implants (i.e., any of those referenced in the references incorporated by reference above) or any other implant which may be delivered from a needle or tube-like structure.

The snoring sound may be generated by impulses caused by rapid obstruction and opening of airways. Huang, et al. id., state the airway passage opening and closing occurs 50 times per second during a snore. Huang, et al. id., utilize a spring-mass model to illustrate oscillation of the soft palate in response to airflow (where the soft palate is the ball of mass hanging by a spring from a fixed anchor) as described in the references incorporated by reference above.

Figure 3:
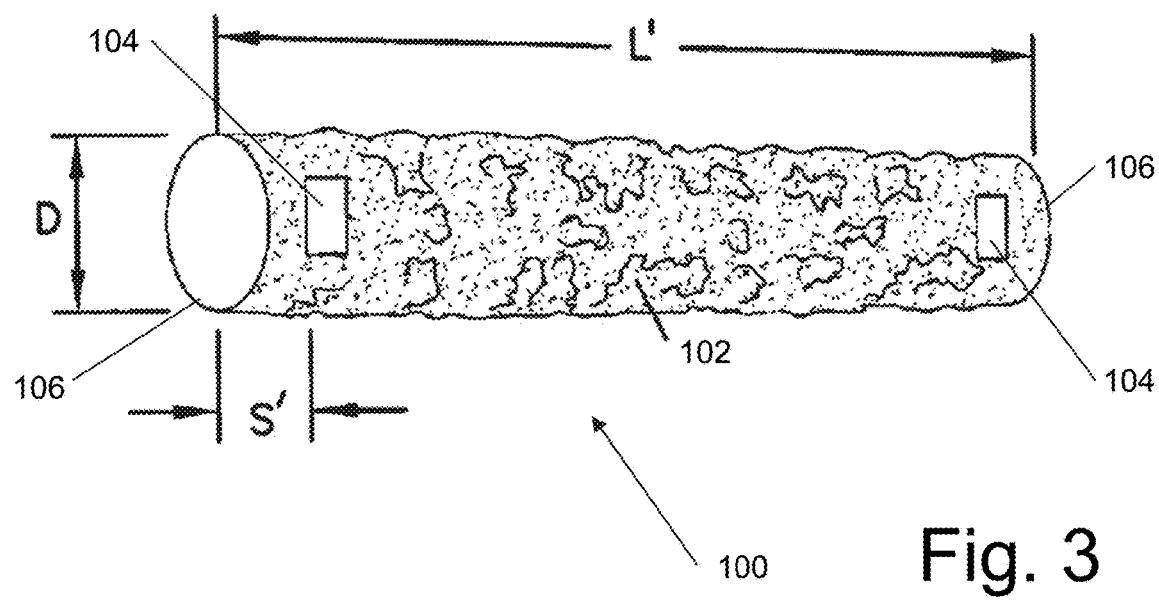
FIG. 3 is a perspective illustration of an implant 100 to be inserted into the soft palate.

In one aspect illustrated in FIG. 3, an implant 100 may be formed from a braid of fibers 102. While a single type fiber could be used in the implant 100, the implant may also be formed of two or more different fibers braided or twisted together. For example, one fiber may be provided for encouraging fibrotic response. Such a fiber may be polyester or silk suture material. The other fiber may be a bio-resorbable fiber (e.g., bio-resorbable suture material which may include natural materials such as collagen or synthetic materials such as the PDS suture material). Alternatively, the other fiber may be a non-resorbable material such as polypropylene suture material to provide added stiffness to the implant 100.

In one embodiment, the implant 100 may be a composite braid of both air-textured and non-air-textured yarns of polyester formed in a braid of about 2 mm in diameter (D) and 18 mm in length (L'). Welds 104 may be formed near the ends 106 of the implant 100 to bond the fibers 102. The welds 104 are spaced from the ends 106 by a spacing S' so that the fibers 102 in the spacing are free to fray and present a fluffier area for tissue in-growth. The implant 102 may be fibrosis inducing to induce a fibrotic response of tissue following implantation. An implant having the foregoing characteristics is more fully described in the aforementioned U.S. Pat. No. 6,513,530.

Figure 4:
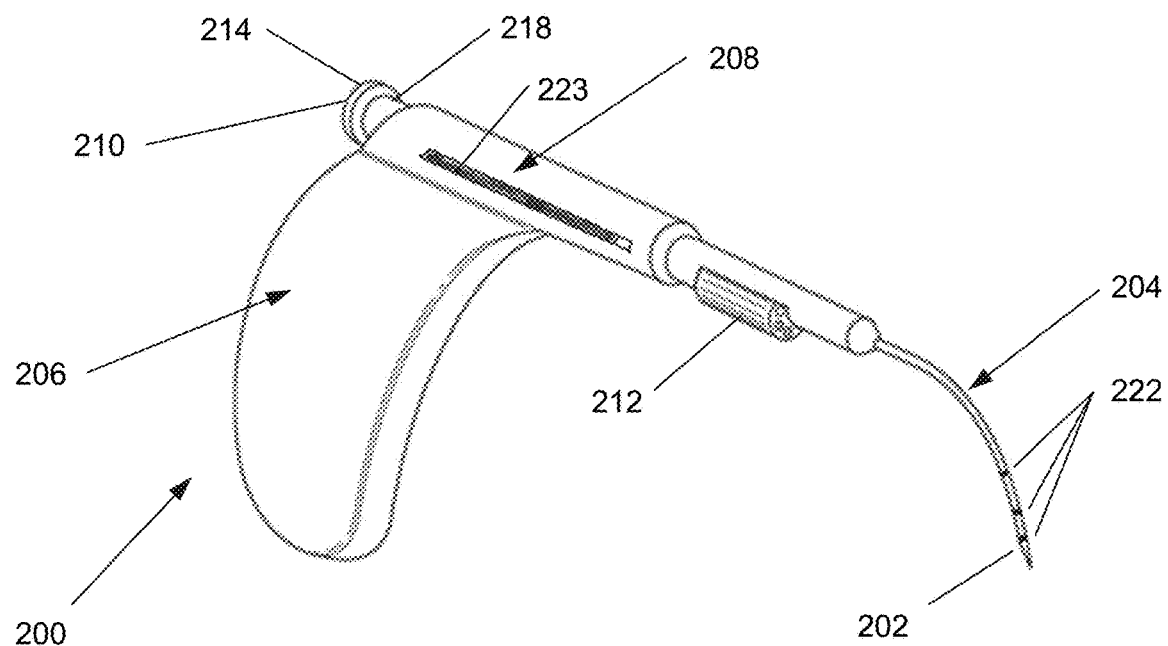
FIG. 4 is an isometric drawing of one embodiment of a delivery tool for placing multiple implants into the soft palate.

FIG. 4 is an isometric drawing of one embodiment of a delivery tool 200 for placing the implant 100 (FIG. 3) in the soft palate SP (FIG. 1). The delivery tool 200 includes a handle portion 206, a barrel portion 208, and a penetrating cannula or delivery needle 204. The delivery needle 204 is hollow and carries the implant 100 in sliding close tolerance especially at a distal end or tip 202. In certain embodiments, the delivery needle 204 is bent to permit ease of placement of the distal tip 202 into the soft palate SP without interference of the tool with the patient's teeth or hard palate. The delivery needle 204 has markings 222 to provide an indication to an operator of depth of penetration of the distal tip 202 in tissue. Some embodiments may have corresponding markings or a visual indicator 223 placed on the barrel portion 208 or on slider 218 of an actuator 210 to indicate the implant position 100 relative to the distal tip 202 of the delivery needle 204 when the implant is in the delivery needle.

Figure 5:
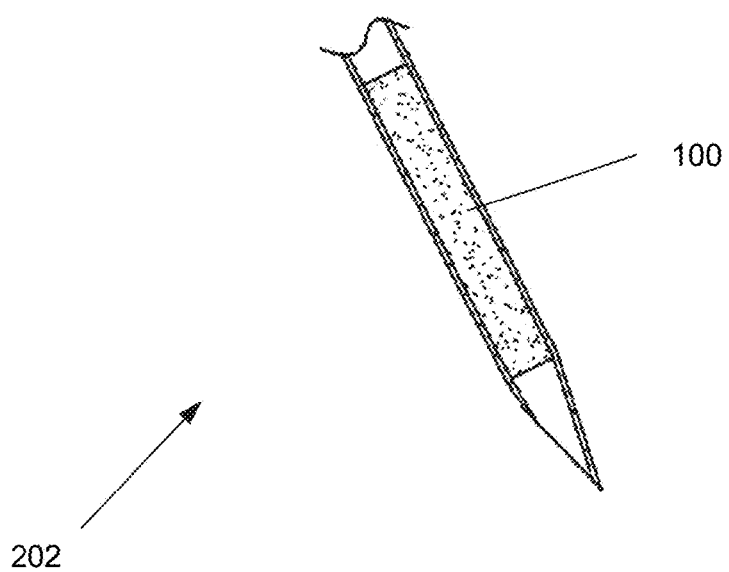
FIG. 5 is a detailed section view of one embodiment of the distal tip of the delivery tool illustrated in FIG. 4.

FIG. 5 is a detailed section view of one embodiment of the distal tip 202 of a delivery needle 204, showing the implant 100 positioned within the delivery needle as the implant is about to be placed into the patient. In the illustrated embodiment, the distal tip 202 of needle 204 has a bevel ground for piercing tissue of the soft palate.

The handle 206 is designed to be hand-grasped in a pistol-grip manner and is coupled to the barrel portion 208. The barrel portion 208 engages the sliding actuator 210. In certain embodiments, the proximal end of the sliding actuator includes a thumb rest 214 positioned to oppose the operator's thumb (not shown) when the handle portion 206 is grasped. In certain embodiments, an engagement mechanism (not shown), such as removable tape engages the actuator 210 during shipping and storage to prevent undesired movement of the actuator 210. In the embodiment illustrated in FIG. 4, there is also a cylindrical cartridge 212 which contains a plurality of implants 100 (not shown).

Figure 6A:
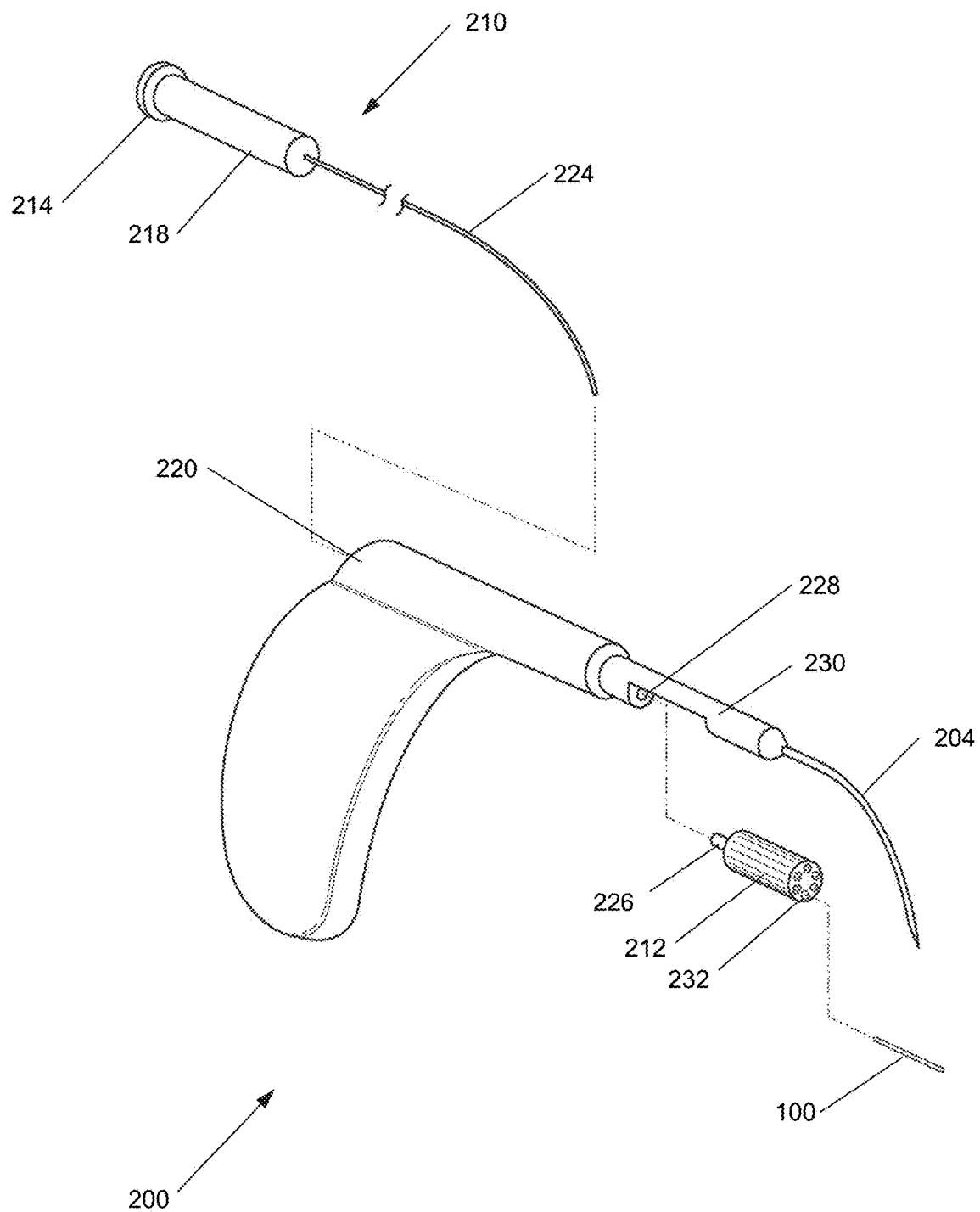
FIG. 6A illustrates an exploded isometric view of the delivery tool of FIG. 4.
Figure 6B:
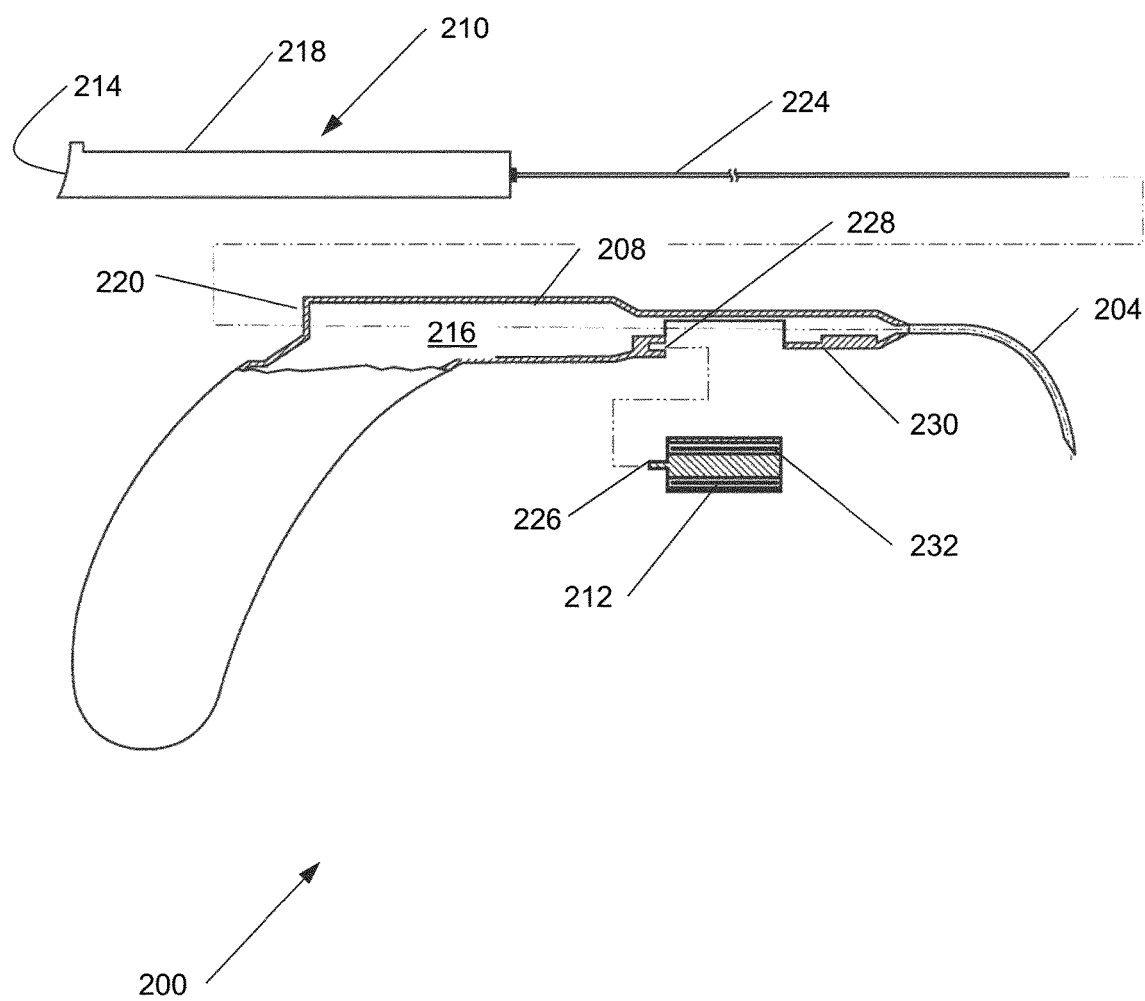
FIG. 6B is an exploded sectional view of the delivery tool of FIG. 4.

FIG. 6A illustrates an exploded isometric view of the delivery tool 200 with the actuator 210 and the cylindrical cartridge 212 removed from the delivery tool 200. FIG. 6B is an exploded sectional view of the delivery tool 200 with the actuator 210 and cylindrical cartridge also removed for clarity. As illustrated in FIGS. 6A and 6B, the actuator 210 comprises a thumb rest 214 coupled to a proximal end of a large obturator or slider 218. A distal end of the slider 218 is coupled to a proximal end of smaller flexible rod or obturator 224. The obturator 224 is sized to slidingly fit within the delivery needle 204. The diameter of the obturator 224 is such that it is sufficient for pushing against an implant 100 when the implant 100 is also positioned within the delivery needle 204 (as illustrated in FIG. 5). The slider 218 slidingly engages a barrel 216 defined within the barrel portion 208 of the delivery tool 200. In this embodiment, a proximal end 220 of the barrel portion 208 is above the handle portion, in other embodiments the barrel portion 208 (or a portion of the barrel portion) extends in a proximal direction beyond the hand portion 206 to serve to stabilize and guide the slider 218 when the actuator 210 is in an un-actuated or unloaded configuration as discussed below.

The cylindrical cartridge 212 rotates around a pin 226 which rotates within and engages at least one cylindrical aperture 228 defined within a cartridge holding portion 230 of the delivery tool 200. In certain embodiments, the cartridge holding portion may be an elongated member a portion of which is shaped to hold a cartridge 212 and contains a bore for allowing the implant 100 and obturator 224 to be pushed through. In certain embodiments, at least one detent (not shown) defined in the cartridge holding portion 230 or the cylindrical cartridge 212 catches on a protrusion on an opposing surface to prevent the cylindrical cartridge from spinning or rotating freely. The cylindrical cartridge 212 is sized to hold a predetermined number of implants 100. Each implant is positioned inside a bore 232 defined with the cylindrical cartridge 212.

Operation of the First Embodiment

Referring now to FIGS. 7A through 11B, the manner of using one embodiment of the present invention will now be described. Before the implant is inserted, a physician or user typically prepares a patient in a manner known in the art. For instance, an appropriate broad-spectrum antibiotic may be given to the patient both pre- and post-operatively. An oral antiseptic (e.g., chlorhexidine gluconate 0.12%-0.2%) may then be applied to the injection or insertion site IS (see FIG. 11A). The site may then be injected with a local anesthetic (2-3 cc). For instance, nine injections 1 cm apart, starting 1 mm anterior to the hard palate junction. However, excessive anesthetic may cause tissue ballooning which may affect the implant placement.

Figure 11A:
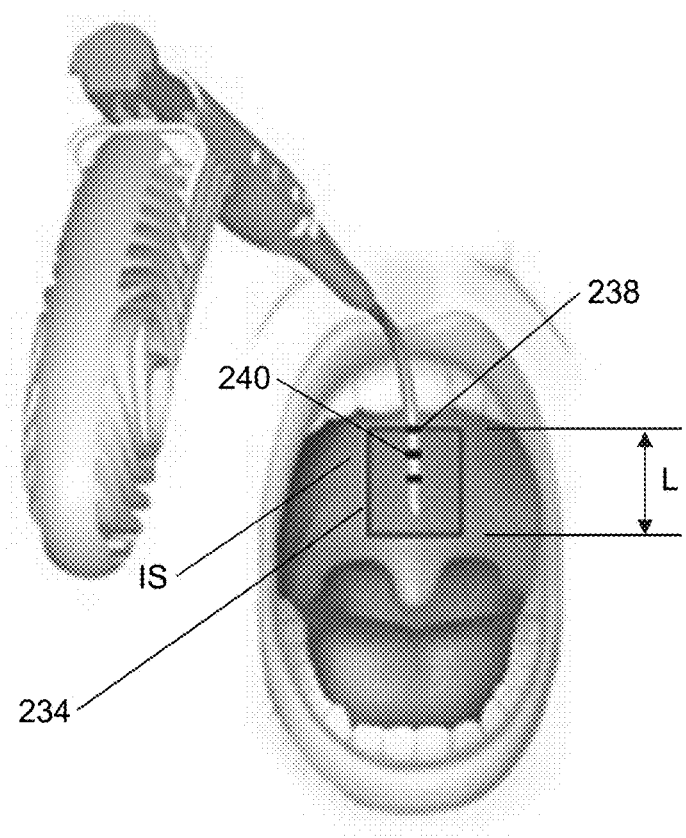
FIG. 11A is a perspective view of one embodiment of a delivery tool with a delivery needle positioned in a patient's air cavity.

A physician may then determine the initial insertion point and measures to ensure palate area length L is at least 25 mm long (see FIG. 11A). The length L may be measured using the markings on the delivery needle to determine the insertion point. The physician may also determine target zone 234 for midline and lateral implant placements (see FIG. 11A).

Figure 7A:
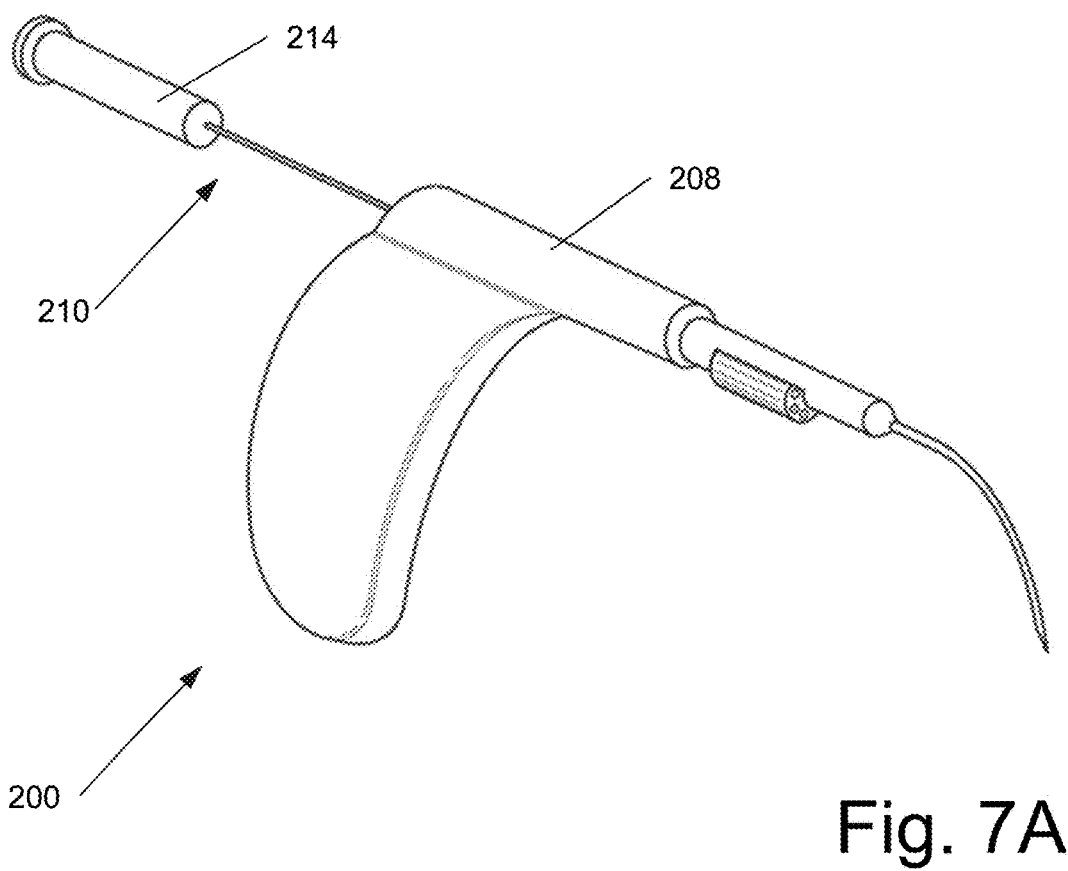
FIG. 7A illustrates an isometric view of the delivery tool of FIG. 4 in an unloaded or first configuration.
Figure 7B:
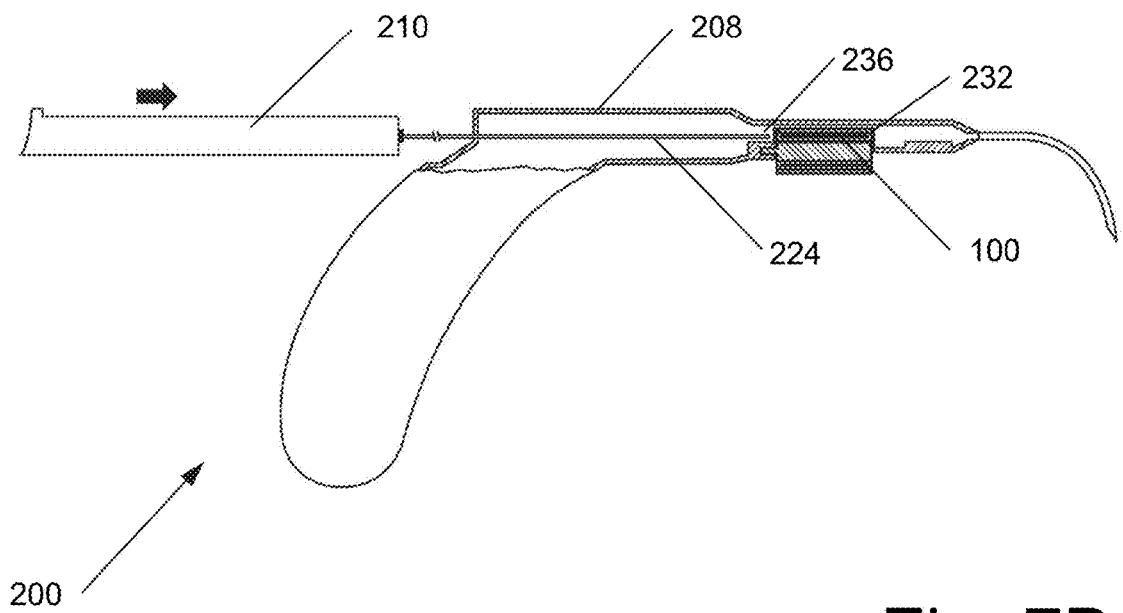
FIG. 7B is a sectional view of the delivery tool of FIG. 4 also in an unloaded or first configuration.

On embodiments having transport lock mechanisms, the transport lock mechanism may be removed by the physician. FIG. 7A illustrates an isometric view of the delivery tool 200 in an unloaded or first configuration. FIG. 7B is a sectional view of the delivery tool 200 also in an unloaded or first configuration. FIGS. 7A and 7B shows a configuration or position where the slider 218 has been pulled or positioned by the physician such that a distal end of the obturator 224 is on the proximal side of the cylindrical cartridge 212 as illustrated in FIG. 7B. The bore 232 contains an implant 100 and is aligned with the distal end 236 of the obturator 224. The user may then push on the slider 218, which in turn, causes the obturator 224 to push the implant 100 out of the bore 232 and into the delivery needle 204. Once the implant 100 has been positioned within the delivery needle 204, a portion of the obturator 224 is also now positioned within the delivery needle 204 and is ready to press against the implant once the delivery needle 204 is inserted into the target zone. Such a "loaded" configuration is illustrated in FIGS. 8A and 8B.

Figure 8A:
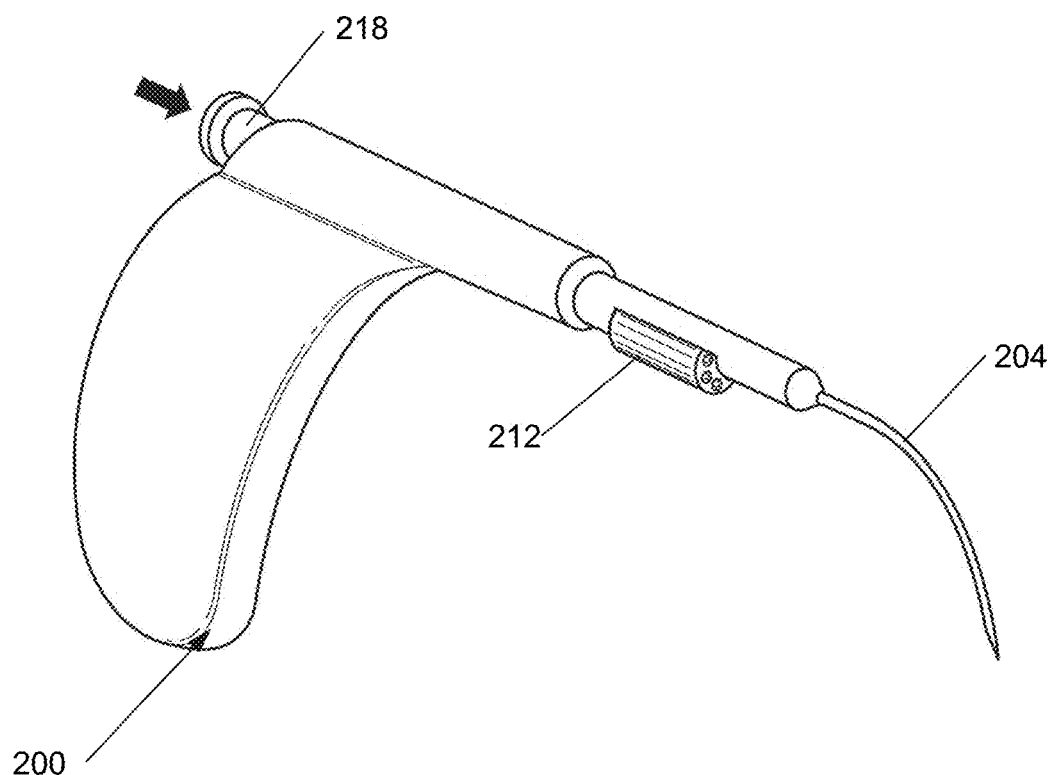
FIG. 8A illustrates an isometric view of the delivery tool of FIG. 4 in a loaded or second configuration.
Figure 8B:
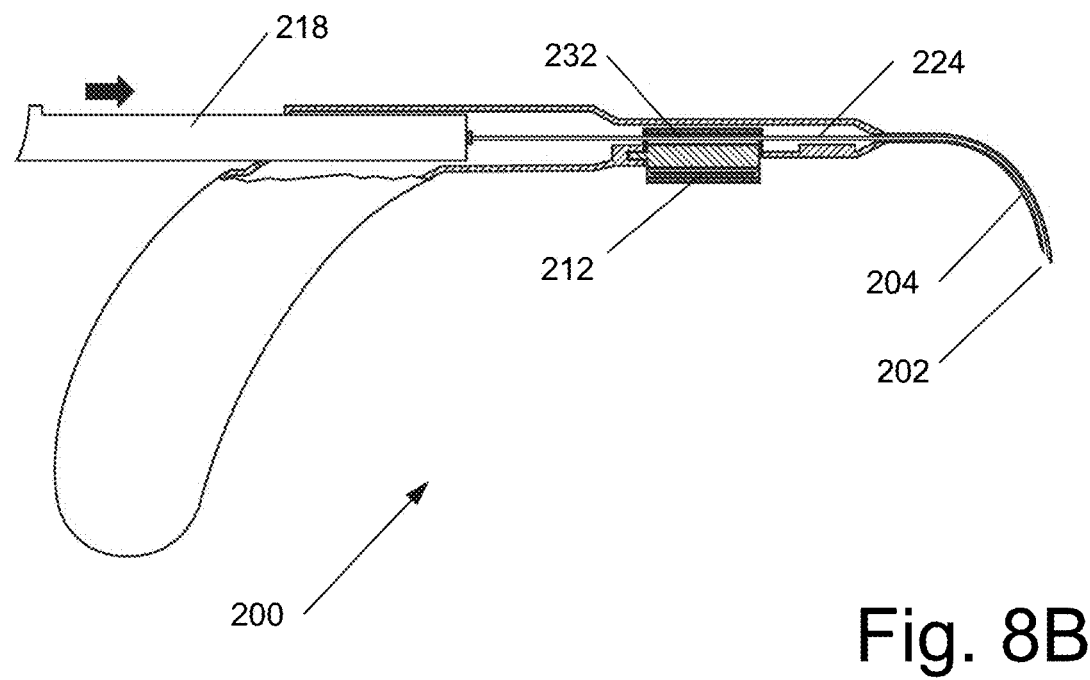
FIG. 8B is a sectional view of the delivery tool of FIG. 4 also in a loaded or second configuration.

FIG. 8A illustrates an isometric view of the delivery tool 200 in a loaded or second configuration (i.e., the implant 100 has been pushed into the delivery needle 204). FIG. 8B is a sectional view of the delivery tool 200 also in a loaded or second configuration. In the configuration illustrated in FIGS. 8A and 8B, the obturator 224 has been pushed through the bore 232 of the cylindrical cartridge 212 and into the delivery needle 204. Such a position may be indicated by the relative distance between the slider 218 and barrel 216 via the barrel indicator 223 (FIG. 4). Thus, this position is shown on the barrel indicator 223 as in the "loaded" or "start" position. In this position, the implant 100 has also been pushed into the delivery needle 204.

To insert the delivery needle into the patient's tissue, the distal tip 202 may then be placed needle high in the palate. Insertion points are to be close to the junction of the hard and soft palate 1 mm anterior to the junction is ideal. This placement in effect extends the length of the hard palate, reducing the palate's tendency to vibrate or obstruct the airway during sleep.

Once the distal tip 202 is in position, the physician can insert the distal tip into the insertion point and continue to drive the delivery needle into the palate until the last or proximal insertion marking 238 is reached (see FIG. 10A). Before deployment of the implant, the physician can confirm proper placement by "tug and wiggle" technique. When using a gentle tug, tenting of the mucosa may indicate an implant placement that is too shallow. A slight wiggle from the ten o'clock to two o'clock position (if thumb is pointing at the 12) should gently shift the soft palate from side to side. This movement helps ensure the implant is placed at the correct depth. If after implant deployment no resistance is felt, the implant may be placed too deep and into the nasopharynx region.

When the delivery tool 200 is in the start configuration after the delivery needle insertion, the implant 100 can then be inserted into tissue by advancing the slider 218 from the start position as indicated on the barrel indicator 223. The physician may stop advancing the slider 218 when it reaches the "halfway deployment" position. In some embodiments, the user may hear an audible "click" and receive tactile feedback indicating the halfway deployment position. In certain embodiments, the audible click may be caused by a combination of one or more detents mating with one or more protrusions on opposing surfaces of the slider 218 and the barrel 216. Additionally, the barrel indicator 223 may also indicate that the slider 218 is in the halfway deployment position. At this position, the delivery needle 204 may be withdrawn until the halfway depth marker 240 on the needle is visible (FIG. 11A).

When the halfway depth marker on the needle is visible, the slider 218 may be advanced until the slider 218 comes to a stop at the "full deployment" position (i.e., the distal tip of the oburator 224 is at (or proximal to) the distal tip 202 of the delivery needle 204). When advancing the slider into the full deployment position, the contact of the implant with tissue at the distal end of the needle track may result in a feeling of resistance and naturally cause the needle tip to push up or out. After the implant is fully deployed, withdraw the delivery needle 204 from the palate following the insertion path (move the handle portion 206 in an arcing fashion).

Once the delivery needle 204 has been completely withdrawn from the patient, the slider 218 may be removed or partially removed from the barrel 216 so that the obturator 224 can be withdrawn from both the delivery needle 204 and the bore 232 of the cylindrical cartridge as discussed above in reference to FIGS. 7A and 7B.

Figure 9A:
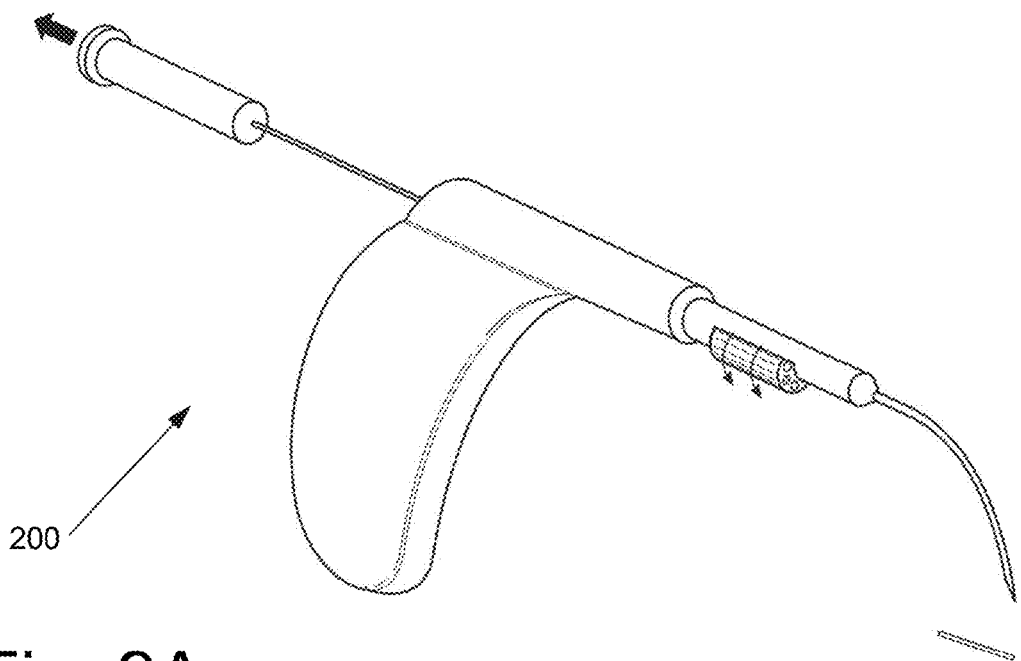
FIG. 9A illustrates an isometric view of the delivery tool of FIG. 4 in an unloaded or first configuration.
Figure 9B:
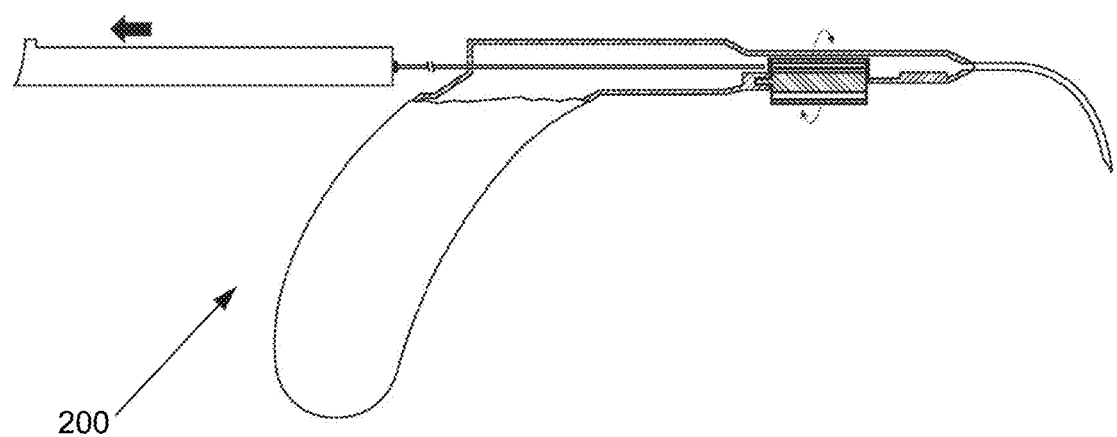
FIG. 9B is a sectional view of the delivery tool of FIG. 4 also in an unloaded or first configuration.

The physician may then rotate the cylindrical cartridge 212 about the pin 226 to align the next bore 232 containing a second implant 100 as indicated in FIGS. 9A and 9B. In certain embodiments, the user may feel or hear a click sound when the cylindrical cartridge 212 has been rotated so that the next bore 232 is aligned with both the obturator 224 and the delivery needle 204. In certain embodiments, the clicking sound may be caused by a combination of one or more detents mating with one or more protrusions on opposing surfaces of the cylindrical cartridge 212 and the cartridge holding portion 230 of the delivery tool 200. The delivery tool 200 is now again in the unloaded or first configuration as described in reference to FIGS. 7A and 7B. The process may now be repeated as described above to insert a second, third, fourth, or even a fifth implant.

For instance, the physician can now move the slider back into the position illustrated by FIGS. 8A and 8B which illustrate the delivery tool 200 in the loaded or second configuration. Thus, the obturator 224 has once again been pushed through the bore 232 of the cylindrical cartridge 212 and into the delivery needle 204 and a second implant 100 has also been pushed into the delivery needle 204 to the appropriate position. As explained above, this position may be shown on the barrel indicator 223 as in the "loaded" or "start" position. The second implant 100 is now ready to be inserted into the patient as explained above.

Figure 10:
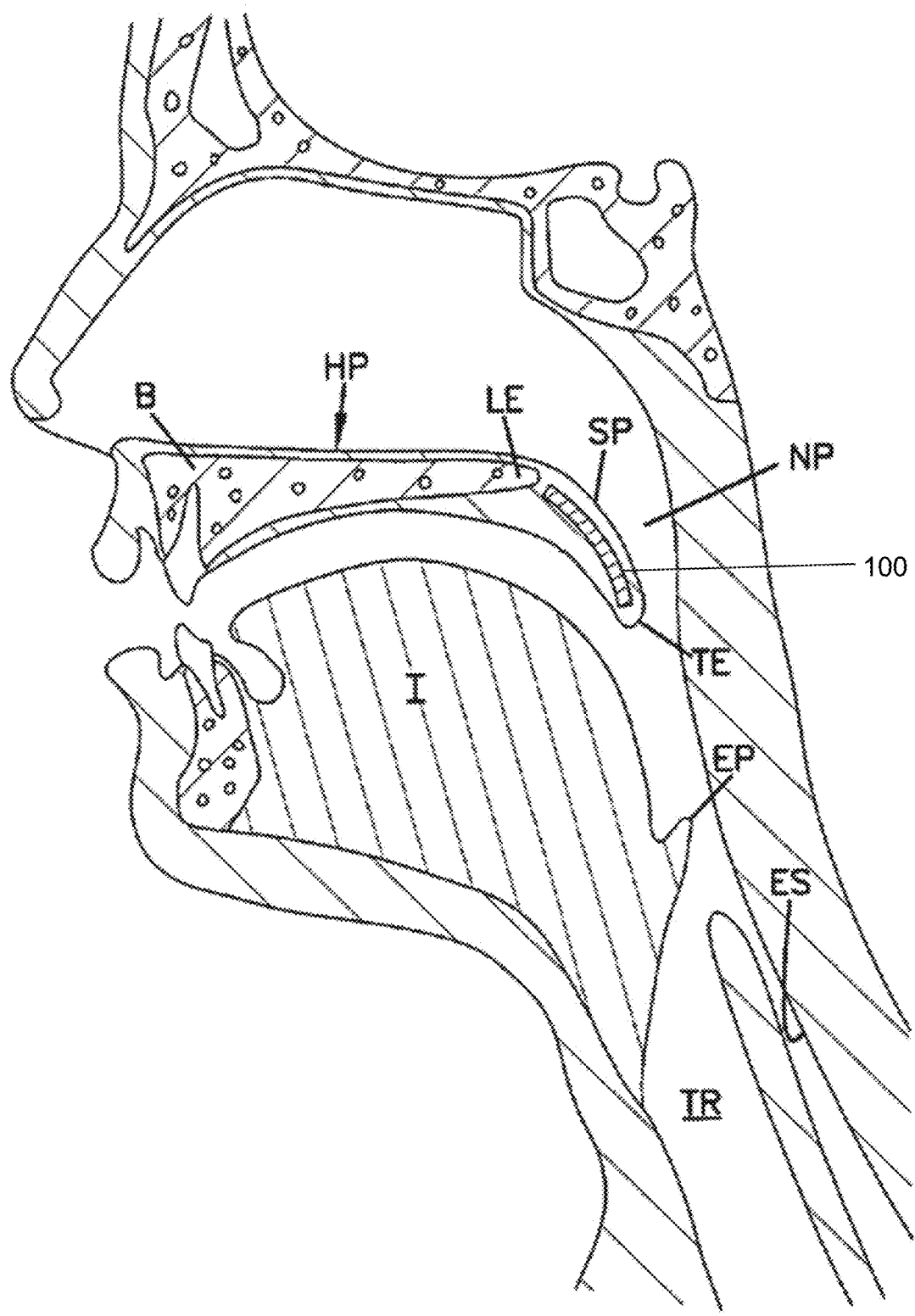
FIG. 10 is a cross-section schematic illustration of a naso-pharyngeal area of a treated patient showing the placement of one or more implants positioned in the soft palate.
Figure 11B:
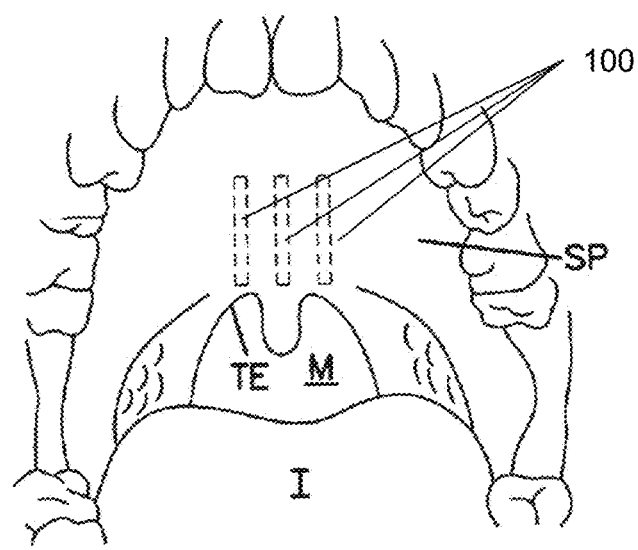
FIG. 11B is a schematic illustration of a soft palate viewed through an open mouth of a treated patient showing the placement of three implants.

FIG. 10 illustrates in cross-section, the naso-pharyngeal area of the patient of FIG. 1 with an implant 100 placed into the soft palate SP according to the above described process. In contrast, FIG. 11B illustrates an embodiment where three implants 100 are placed in the soft palate SP. In the example of FIG. 11B, one implant 100 has been placed at the soft palate midline and one each on opposite sides of the midline about 5 mm from the midline. In other embodiments, the implants may be of different lengths. In yet other embodiments, four or five implants can be placed in the soft palate SP.

Description of a Second Embodiment

Figure 12A:
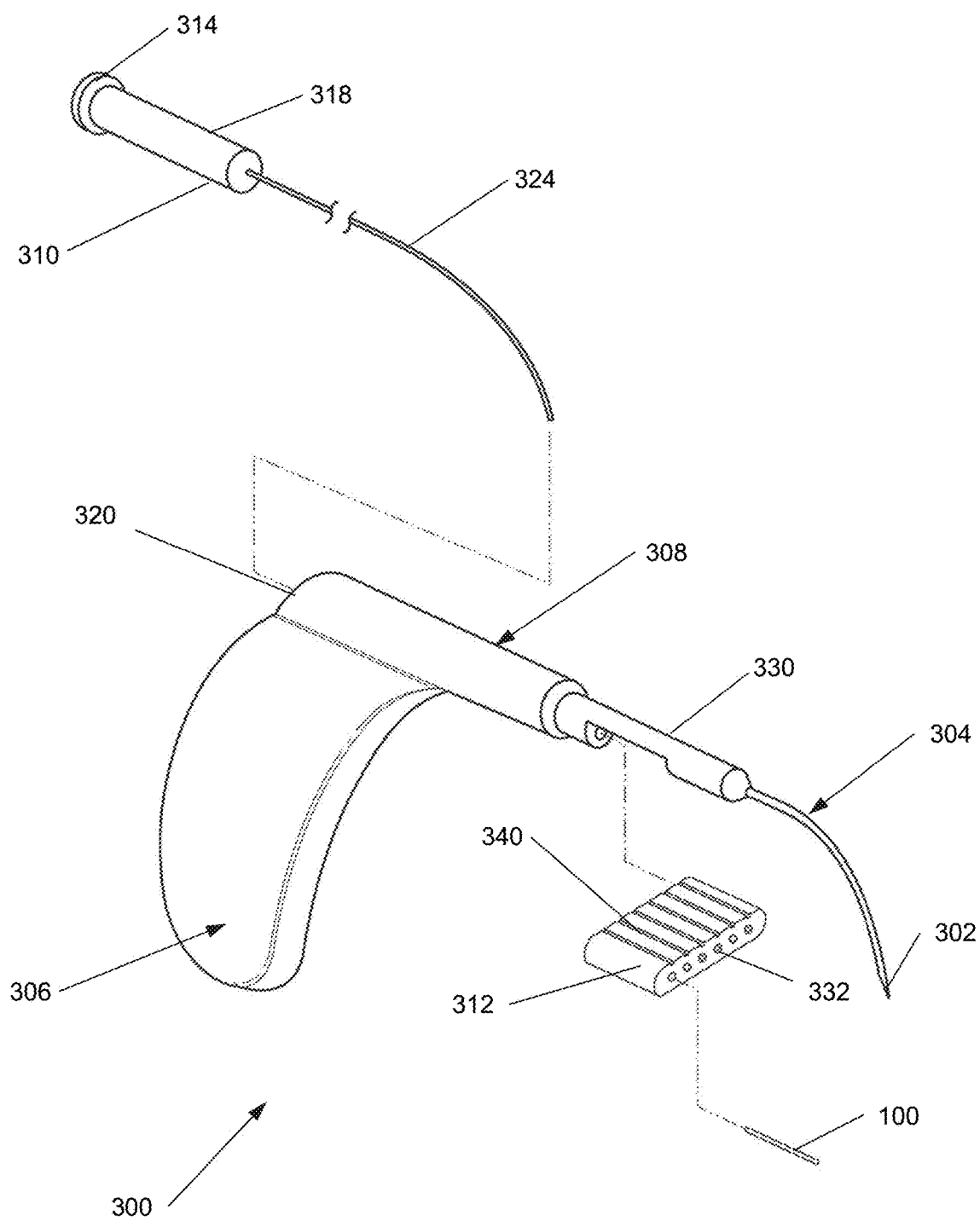
FIG. 12A illustrates an exploded isometric view of second embodiment of a delivery tool.
Figure 12B:
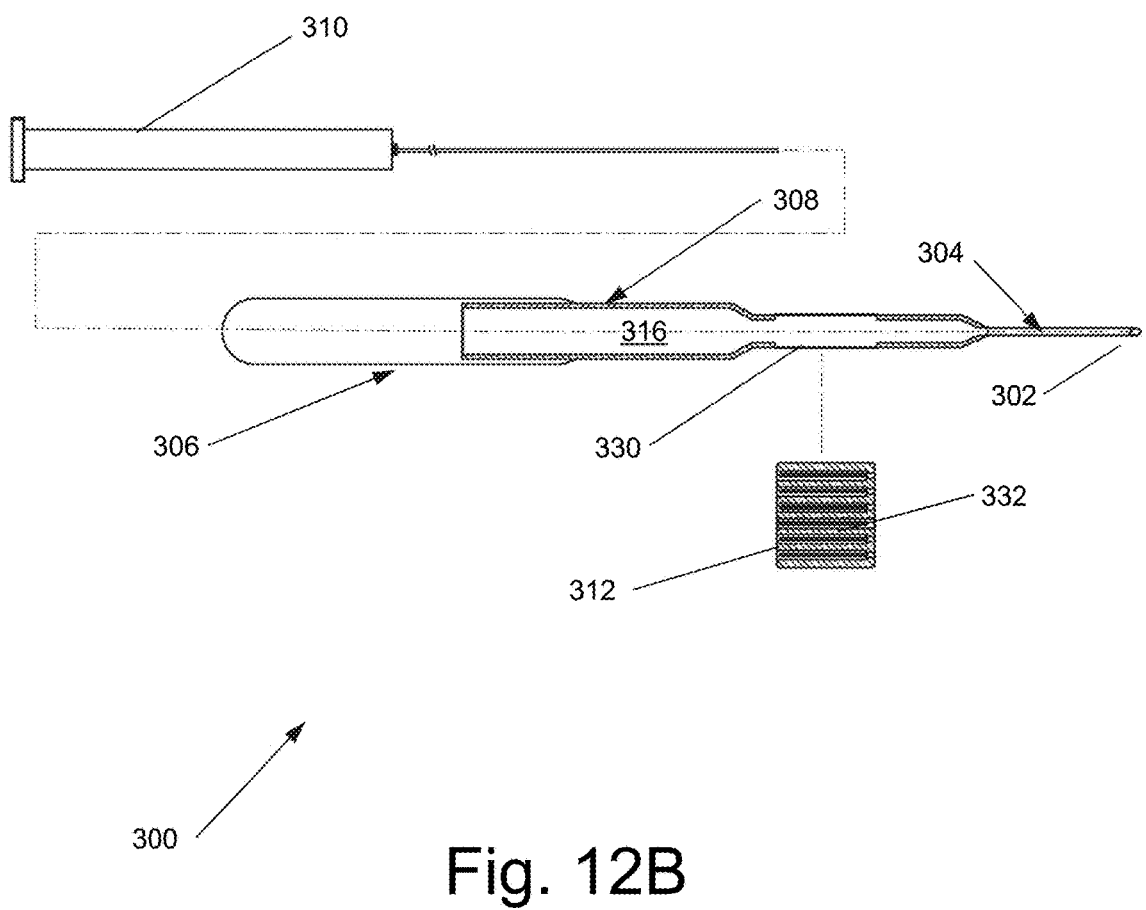
FIG. 12B is an exploded horizontal sectional view of the delivery tool of FIG. 12A.

A second embodiment is illustrated in FIGS. 12A-12B which are figures relating to a second embodiment. The second embodiment is similar to the first embodiment except that a delivery tool 300 uses magazine cartridge 312 in place of the cylindrical cartridge 212.

For brevity and clarity, a description of those parts which are similar or identical to those described in connection with the first embodiment illustrated in FIGS. 1 and 11B may not be repeated here. Reference should be made to the entire application to arrive at a complete understanding of this second embodiment.

FIG. 12A is an isometric exploded drawing of the second embodiment of the delivery tool 300 for placing the implant 100 (FIG. 3) in the soft palate SP (FIG. 1). FIG. 12B is a horizontal section exploded view of the delivery tool 300. Turning to both FIGS. 12A and 12B, the delivery tool 300 includes a handle portion 306, a barrel portion 308, and a delivery needle 304. As in the first embodiment, the delivery needle 304 is hollow and carries the implant 100 in sliding close tolerance especially at a distal end or tip 302. In certain embodiments, the delivery needle 304 is bent to permit ease of placement of the distal tip 302 into the soft palate SP without interference of the tool with the patient's teeth or hard palate. The delivery needle 304 has markings (see markings 222 of FIG. 4) to provide an indication to an operator of depth of penetration of the distal tip 302 in tissue. Some embodiments may have corresponding markings or a visual indicator placed on the barrel portion or on slider of an actuator 310 to indicate the implant position 100 relative to the distal tip 302 of the delivery needle 304 when the implant is in the delivery needle as explained above in reference to FIG. 4.

The handle 306 is designed to be hand-grasped in a pistol-grip manner and is coupled to the barrel portion 308. The barrel portion 308 engages the sliding actuator 310. In certain embodiments, the proximal end of the sliding actuator includes a thumb rest 314 positioned to oppose the operator's thumb (not shown) when the handle portion 306 is grasped. In certain embodiments, an engagement mechanism (not shown), such as removable tape engages the actuator 310 during shipping and storage to prevent undesired movement of the actuator 310. In the embodiment illustrated in FIGS. 12A and 12B, there is also the magazine cartridge 312 which contains a plurality of implants 100 (one of which is illustrated in FIG. 12A).

In FIGS. 12A and 12B, the actuator 3120 and the magazine cartridge 312 are exploded for clarity. As illustrated in FIGS. 12A and 12B, the actuator 310 comprises a thumb rest 314 coupled to a proximal end of a large obturator or slider 318. A distal end of the slider 318 is coupled to a proximal end of smaller flexible rod or obturator 324. The obturator 324 is sized to slidingly fit within the delivery needle 304. The diameter of the obturator 324 is such that it is sufficient for pushing against the implant 100 when the implant is also positioned within the delivery needle 304 (as illustrated in FIG. 5). The slider 318 slidingly engages a barrel 316 defined within the barrel portion 308 of the delivery tool 300. In this embodiment, a proximal end 320 of the barrel portion 308 is above the handle portion, in other embodiments the barrel portion 308 (or a portion of the barrel portion) extends in a proximal direction beyond the hand portion 306 to serve to stabilize and guide the slider 318 when the actuator 310 is in an unactuated or unloaded configuration as discussed below.

In certain embodiments, the magazine cartridge 312 slides within a groove (not shown) defined within a cartridge holding portion 330 of the delivery tool 300. In certain embodiments, at least one detent 340 defined on a surface of the magazine cartridge 312 (or alternatively in the cartridge holding portion 330) catches on a protrusion on an opposing surface to prevent the magazine cartridge from sliding freely. The magazine cartridge 312 is sized to hold a predetermined number of implants 100. Each implant 100 is positioned inside a bore(s) 332 defined with the magazine cartridge 312.

Operation of the Second Embodiment

Referring now to FIGS. 13A through 15B, the manner of using the second embodiment of the present invention will now be described. Before the implant is inserted, a physician or user typically prepares a patient in a manner known in the art. For instance, an appropriate broad-spectrum antibiotic may be given to the patient both pre- and post-operatively. An oral antiseptic (e.g., chlorhexidine gluconate 0.12%-0.2%) may then be applied to the injection or insertion site IS (see FIG. 11A). The site may then be injected with a local anesthetic (2-3 cc). For instance, nine injections 1 cm apart, starting 1 mm anterior to the hard palate junction. However, excessive anesthetic may cause tissue ballooning which may affect the implant placement.

A physician may then determine the initial insertion point and measures to ensure palate area length L is at least 25 mm long (see FIG. 11A). The length L may be measured using the markings on the delivery needle to determine the insertion point. The physician may also determine target zone 234 for midline and lateral implant placements (see FIG. 11A).

Figure 13A:
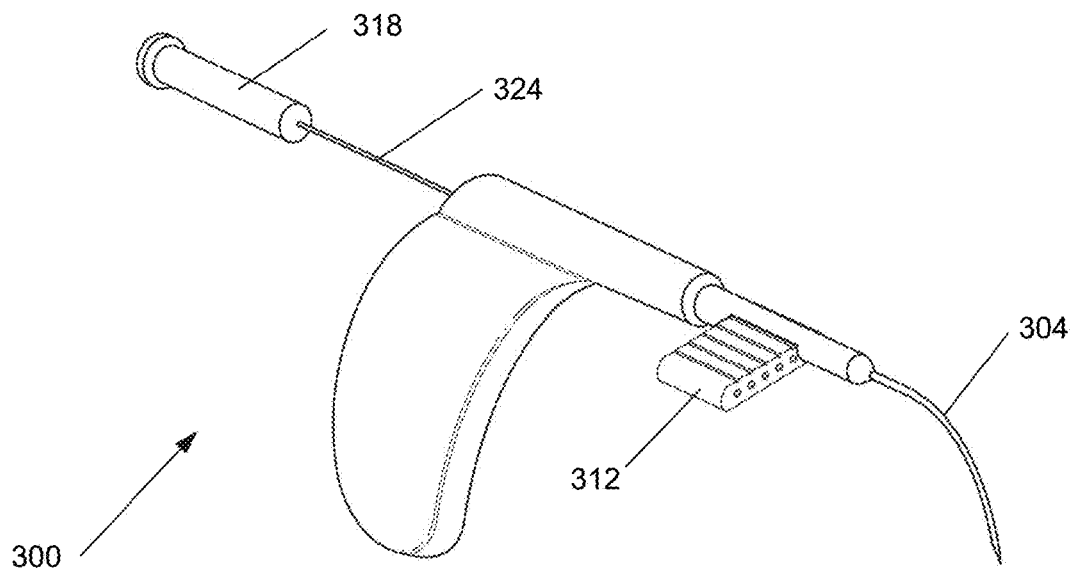
FIG. 13A illustrates an isometric view of the delivery tool of FIG. 12A in an unloaded or first configuration.
Figure 13B:
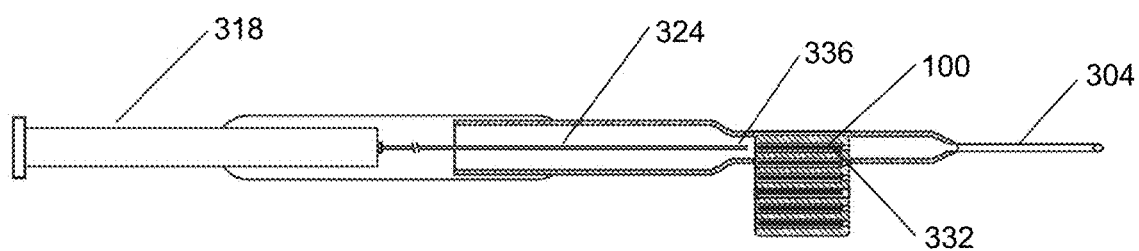
FIG. 13B is a horizontal sectional view of the delivery tool of FIG. 12A also in an unloaded or first configuration.

On embodiments having transport lock mechanisms, the transport lock mechanism may be removed by the physician. FIG. 13A illustrates an isometric view of the delivery tool 300 in an unloaded or first configuration. FIG. 13B is a horizontal sectional view of the delivery tool 300 also in an unloaded or first configuration. FIGS. 13A and 13B shows a configuration or position where the slider 318 has been pulled or positioned by the physician such that a distal end 336 of the obturator 324 is on the proximal side of the magazine cartridge 312 as illustrated in FIG. 13B. As illustrated in FIG. 13B, the bore 332 contains an implant 100 and is aligned with the distal end 336 of the obturator 324. The user may then push on the slider 318, which in turn, causes the obturator 324 to push the implant 100 out of the bore 332 and into the delivery needle 304. Once the implant 100 has been positioned within the delivery needle 304, a portion of the obturator 324 is also now positioned within the delivery needle 304 and is ready to press against the implant once the delivery needle 304 is inserted into the target zone. Such a "loaded" configuration is illustrated in FIGS. 14A and 14B.

Figure 14A:
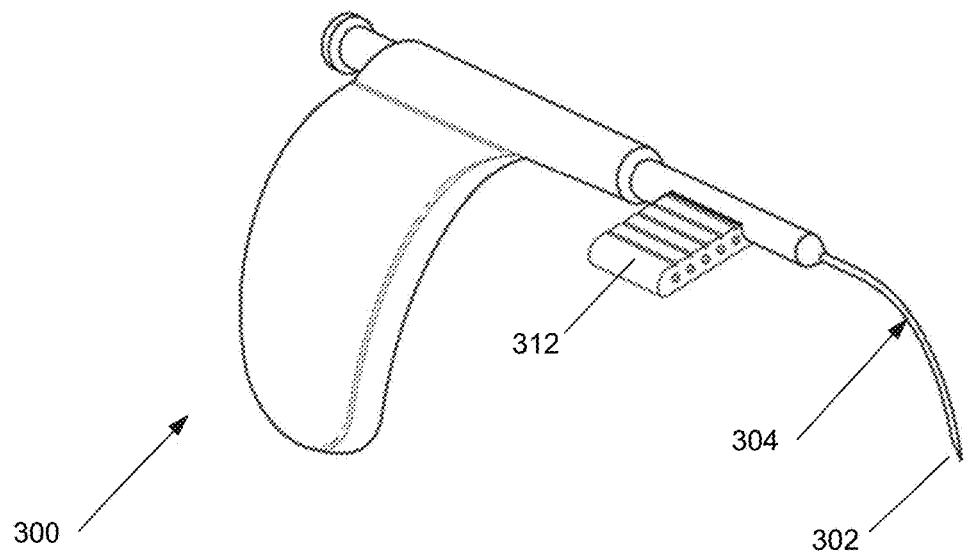
FIG. 14A illustrates an isometric view of the delivery tool of FIG. 12A in a loaded or second configuration.
Figure 14B:
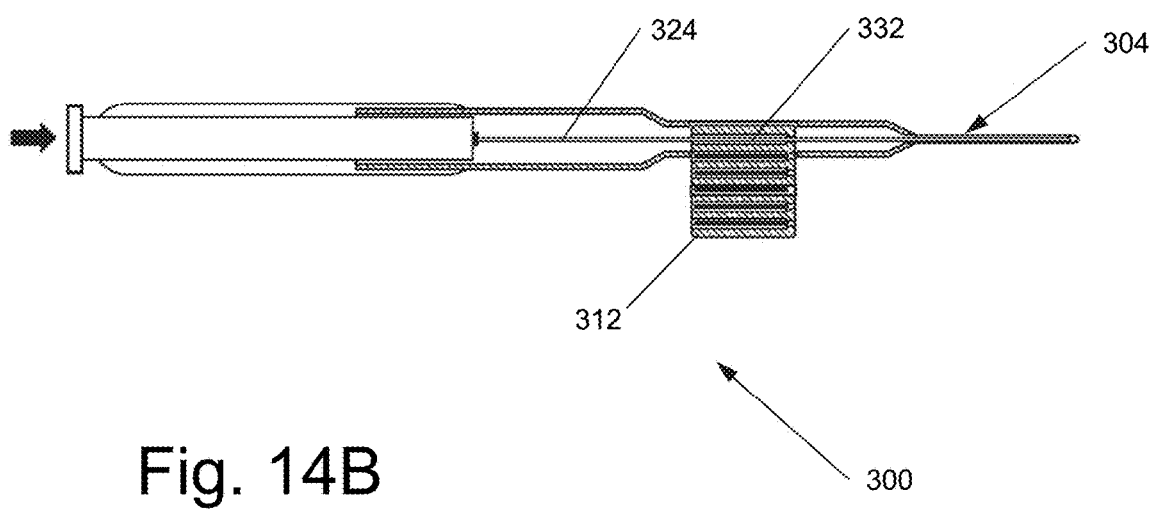

FIG. 14A illustrates an isometric view of the delivery tool 300 in a loaded or second configuration (i.e., the implant 100 has been pushed into the delivery needle 304). FIG. 14B is a sectional view of the delivery tool 300 also in a loaded or second configuration. In the configuration illustrated in FIGS. 14A and 14B, the obturator 324 has been pushed through the bore 332 of the magazine cartridge 312 and into the delivery needle 304. Such a position of the slider 318 and implant 100 may be indicated by the relative distance between the slider 318 and barrel 316 via the barrel indicator 323 (FIG. 4). Thus, this position may be shown on the barrel indicator 323 (FIG. 4) as in the "loaded" or "start" position.

To insert the delivery needle into the patient's tissue, the distal tip 302 may then be placed needle high in the palate. Insertion points are to be close to the junction of the hard and soft palate 1 mm anterior to the junction is ideal. This placement in effect extends the length of the hard palate, reducing the palate's tendency to vibrate or obstruct the airway during sleep.

Once the distal tip 302 is in position, the physician can insert the distal tip into the insertion point and continue to drive the delivery needle into the palate until the last or proximal insertion marking 338 is reached (see FIG. 10A). Before deployment of the implant, the physician can confirm proper placement by "tug and wiggle" technique. When using a gentle tug, tenting of the mucosa may indicate an implant placement that is too shallow. A slight wiggle from the ten o'clock to two o'clock position (if thumb is pointing at the 12) should gently shift the soft palate from side to side. This movement helps ensure the implant is placed at the correct depth. If after implant deployment no resistance is felt, the implant may be placed too deep and into the nasopharynx region.

When the delivery tool 300 is in the start configuration after the delivery needle insertion, the implant 100 can then be inserted into tissue by advancing the slider 318 from the start position as indicated on the barrel indicator 323. The physician may stop advancing the slider 318 when it reaches the "halfway deployment" position. In some embodiments, the user may hear an audible "click" and receive tactile feedback indicating the halfway deployment position. In certain embodiments, the audible click may be caused by a combination of one or more detents mating with one or more protrusions (not shown) on opposing surfaces of the slider 318 and the barrel 316. Additionally, in some embodiments, the barrel indicator 323 may also indicate that the slider 318 is in the halfway deployment position. At this position, the delivery needle 304 may be withdrawn until the halfway depth marker 340 on the needle is visible (FIG. 11A).

When the halfway depth marker on the needle is visible (see FIG. 11A), the slider 318 may be advanced until the slider 318 comes to a stop at the "full deployment" position (i.e., the distal tip of the oburator 324 is at (or proximal to) the distal tip 302 of the delivery needle 304). When advancing the slider into the full deployment position, the contact of the implant with tissue at the distal end of the needle track may result in a feeling of resistance and naturally cause the needle tip to push up or out. After the implant is fully deployed, withdraw the delivery needle 304 from the palate following the insertion path (move the handle portion 306 in an arcing fashion).**

Once the delivery needle 304 has been completely withdrawn from the patient, the slider 318 may be removed or partially removed from the barrel 316 so that the obturator 324 can be withdrawn from both the delivery needle 304 and the bore 332 of the magazine cartridge 312 as discussed above in reference to FIGS. 13A and 13B.

Figure 15A:
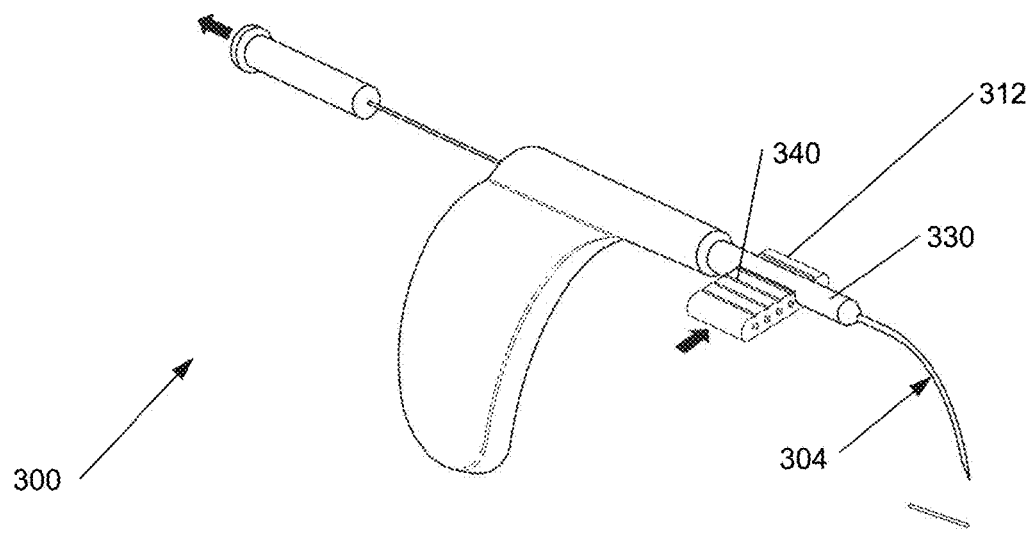
FIG. 15A illustrates an isometric view of the delivery tool of FIG. 12A in an unloaded or first configuration.
Figure 15B:
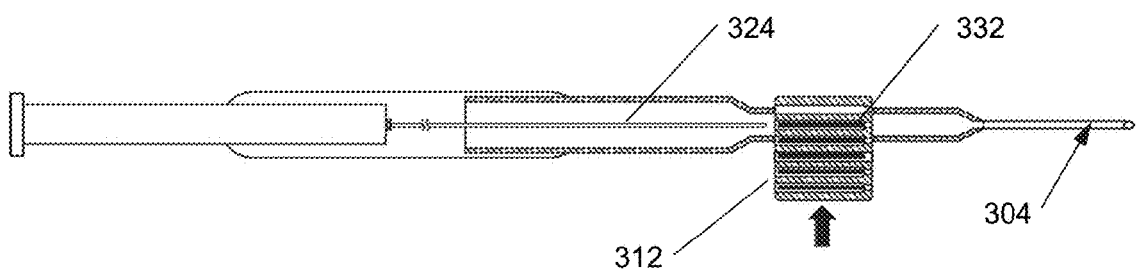
FIG. 15B is a sectional view of the delivery tool of FIG. 12A also in an unloaded or first configuration.

The physician may then slide the magazine cartridge 312 to align the next bore 332 containing a second implant 100 as indicated in FIGS. 15A and 15B. In certain embodiments, the user may feel or hear a click sound when the magazine cartridge 312 has been pushed into position so that the next bore 332 is aligned with both the obturator 324 and the delivery needle 304. In certain embodiments, the clicking sound may be caused by a combination of one or more detents 340 mating with one or more protrusions on opposing surfaces of the magazine cartridge 312 and the cartridge holding portion 330 of the delivery tool 300. The delivery tool 300 is now again in essentially the unloaded or first configuration as described in reference to FIGS. 13A and 13B. The process may now be repeated as described above to insert a second, third, fourth, or even a fifth implant.

For instance, the physician can now move the slider back into the position illustrated by FIGS. 14A and 14B which illustrate the delivery tool 300 in the loaded or second configuration. Thus, the obturator 324 has once again been pushed through the bore 332 of the magazine cartridge 312 and into the delivery needle 304 and a second implant 100 has also been pushed into the delivery needle 304 to the appropriate position. As explained above, this position may be shown on the barrel indicator 323 as in the "loaded" or "start" position as illustrated in FIGS. 14A and 14B. The second implant 100 is now ready to be inserted into the patient as explained above.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112(f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112(f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

The invention claimed is:

1. A delivery tool for delivering a plurality of implants into a soft palate of a patient for treatment of sleep breathing disorders, the delivery tool comprising:
a curved penetrating cannula with a proximal end and a distal tip, wherein a curve of the penetrating cannula approximates a curvature of the soft palate, the distal tip shaped for penetration into the soft palate through a small penetration wound, the penetrating cannula having a plurality of depth markings to provide a visual indication of penetration depth, wherein the plurality of depth markings includes a halfway depth marking that is based on a length of one of the plurality of implants,
a cylindrical cartridge having a plurality of longitudinal bores wherein at least one of the longitudinal bores is adapted to align with the proximal end of the penetrating cannula, and wherein the plurality of longitudinal bores are positioned radially about a longitudinal axis of the cylindrical cartridge,
the plurality of implants, where each implant is positioned within a respective longitudinal bore of the plurality of bores and each implant comprises flexible, fibrous, bio-compatible material,
an obturator sized to fit within the penetrating cannula, the obturator adapted for pushing one of the plurality of implants through the at least one of the longitudinal bores and through the penetrating cannula such that the longitudinal dimension of the implant is aligned with an axis of the penetrating cannula,
an actuator having a distal end coupled to the proximal end of the obturator and a proximal end of the actuator for interacting with a user, and
a deployment indicator positioned to indicate when the obturator is in a halfway deployment position, wherein the halfway deployment position corresponds to the halfway depth marking and indicates when the penetrating cannula is to be withdrawn to the halfway depth marking during delivery of one of the plurality of implants.

2. The delivery tool of claim 1, further comprising a barrel portion sized to allow the actuator to slidingly engage an inside surface of the barrel portion.

3. The delivery tool of claim 2, further comprising a cartridge holding portion positioned between barrel portion and the proximal end of penetrating cannula.

4. The delivery tool of claim 3 further comprising a handle portion having a first surface with a first straight edge and a second surface with a second straight edge, wherein the first and second straight edges are coupled to the barrel portion parallel to a longitudinal axis of the barrel portion, wherein the handle portion is configured to be hand-grasped in a pistol-grip manner.

5. The delivery tool of claim 4 wherein the handle portion is coupled to the barrel portion at an offset from the longitudinal axis.

6. The delivery tool of claim 4 wherein the first surface is curved in a concave manner relative to the first edge, wherein the second surface is curved in a concave manner relative to the second edge, and wherein at least a portion of the first surface is curved to match a portion of the second surface.

7. The delivery tool of claim 6 wherein the first and second surfaces are connected by a third surface, wherein a first portion of the third surface that is proximate to the actuator is curved in a convex manner and a second portion of the third surface that is proximate to the cartridge holding portion is curved in a concave manner.

8. The delivery tool of claim 7 wherein the third surface is substantially perpendicular to the first and second surfaces.

9. The delivery tool of claim 7 wherein the first and second portions of the third surface are angled away from the body portion at an obtuse angle relative to the cartridge holding portion.

10. The delivery tool of claim 7 wherein the first and second edges are coupled together, and wherein the third surface narrows as it approaches the first and second edges.

11. The delivery tool of claim 6 wherein the first surface, the second surface, and the curved penetrating cannula are curved in a single direction relative to the barrel portion.

12. The delivery tool of claim 4 wherein the proximal end of the actuator includes a thumb rest positioned to oppose the user's thumb when the handle portion is grasped.

13. The delivery tool of claim 1 wherein the deployment indicator is a visual indicator positioned on the barrel portion.

14. The delivery tool of claim 1 wherein the deployment indicator is a tactile indicator.

15. The delivery tool of claim 1 wherein each implant has a first end and a second end and is formed by a plurality of fibers, wherein the first end has a first weld coupling the fibers and the second end has a second weld coupling the fibers.

16. The delivery tool of claim 15 wherein the first and second welds are spaced from the first and second ends, respectively.

17. A delivery tool for delivering a plurality of implants into a soft palate of a patient for treatment of sleep breathing disorders, the delivery tool comprising:
- a curved penetrating cannula with a proximal end and a distal tip, wherein a curve of the penetrating cannula approximates a curvature of the soft palate, the distal tip shaped for penetration into the soft palate through a small penetration wound, the penetrating cannula having a plurality of depth markings to provide a visual indication of penetration depth, wherein the plurality of depth markings includes a halfway depth marking that is based on a length of one of the plurality of implants,
- a cylindrical cartridge having a plurality of longitudinal bores wherein at least one of the longitudinal bores is adapted to align with the proximal end of the penetrating cannula, and wherein the plurality of longitudinal bores are positioned radially about a longitudinal axis of the cylindrical cartridge,
- an obturator sized to fit within the penetrating cannula, the obturator adapted for pushing one of the plurality of implants through the at least one of the longitudinal bores and through the penetrating cannula such that the longitudinal dimension of the implant is aligned with an axis of the penetrating cannula,
- an actuator having a distal end coupled to the proximal end of the obturator and a proximal end of the actuator for interacting with a user, and
- a deployment indicator positioned to indicate when the obturator is in a halfway deployment position, wherein the halfway deployment position corresponds to the halfway depth marking and indicates when the penetrating cannula is to be withdrawn to the halfway depth marking during delivery of one of the plurality of implants.

18. The delivery tool of claim 17 further comprising a plurality of implants, where each implant is positioned within a respective longitudinal bore of the plurality of bores and each implant comprises flexible, fibrous, bio-compatible material.

19. The delivery tool of claim 17, further comprising a barrel portion sized to allow the actuator to slidingly engage an inside surface of the barrel portion.

20. The delivery tool of claim 19, further comprising a cartridge holding portion positioned between barrel portion and the proximal end of penetrating cannula.

21. The delivery tool of claim 20 further comprising a handle portion having a first surface with a first straight edge and a second surface with a second straight edge, wherein the first and second straight edges are coupled to the barrel portion parallel to a longitudinal axis of the barrel portion, wherein the handle portion is configured to be hand-grasped in a pistol-grip manner.

22. The delivery tool of claim 21 wherein the handle portion is coupled to the barrel portion at an offset from the longitudinal axis.

23. The delivery tool of claim 21 wherein the first surface is curved in a concave manner relative to the first edge, wherein the second surface is curved in a concave manner relative to the second edge, and wherein at least a portion of the first surface is curved to match a portion of the second surface.

24. The delivery tool of claim 23 wherein the first and second surfaces are connected by a third surface, wherein a first portion of the third surface that is proximate to the actuator is curved in a convex manner and a second portion of the third surface that is proximate to the cartridge holding portion is curved in a concave manner.

25. The delivery tool of claim 24 wherein the third surface is substantially perpendicular to the first and second surfaces.

26. The delivery tool of claim 25 wherein the first and second portions of the third surface are angled away from the body portion at an obtuse angle relative to the cartridge holding portion.

27. The delivery tool of claim 26 wherein the first and second edges are coupled together, and wherein the third surface narrows as it approaches the first and second edges.

28. The delivery tool of claim 27 wherein the first surface, the second surface, and the curved penetrating cannula are curved in a single direction relative to the barrel portion.

29. The delivery tool of claim 25 wherein the proximal end of the actuator includes a thumb rest positioned to oppose the user's thumb when the handle portion is grasped.

30. The delivery tool of claim 17 wherein the deployment indicator is a visual indicator positioned on the barrel portion.

31. The delivery tool of claim 17 wherein the deployment indicator is a tactile indicator.

32. The delivery tool of claim 18 wherein each implant has a first end and a second end and is formed by a plurality of fibers, wherein the first end has a first weld coupling the fibers and the second end has a second weld coupling the fibers.

33. The delivery tool of claim 32 wherein the first and second welds are spaced from the first and second ends, respectively.

* * * * *